(12) United States Patent
Eschelman et al.

(10) Patent No.: US 9,189,941 B2
(45) Date of Patent: Nov. 17, 2015

(54) STEPPED ALARM METHOD FOR PATIENT MONITORS

(75) Inventors: Larry James Eschelman, Ossining, NY (US); Bastiaan Feddes, Bilthoven (NL); Abigail Acton Flower, Crompond, NY (US); Nicolaas Lambert, Waalre (NL); Kwok Pun Lee, Flushing, NY (US); Davy Hin Tjiang Tjan, Bennekom (NL); Stijn De Waele, Ossining, NY (US); Brian David Gross, North Andover, MA (US); Joseph J. Frassica, Gloucester, MA (US); Larry Nielsen, Burlington, MA (US); Mohammed Saeed, Cambridge, MA (US); Hanqing Cao, Nanuet, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 112 days.

(21) Appl. No.: 14/110,715

(22) PCT Filed: Apr. 4, 2012

(86) PCT No.: PCT/IB2012/051654
§ 371 (c)(1),
(2), (4) Date: Oct. 31, 2013

(87) PCT Pub. No.: WO2012/140547
PCT Pub. Date: Oct. 18, 2012

(65) Prior Publication Data
US 2014/0043164 A1 Feb. 13, 2014

Related U.S. Application Data

(60) Provisional application No. 61/475,453, filed on Apr. 14, 2011, provisional application No. 61/578,493, filed on Dec. 21, 2011.

(51) Int. Cl.
*G08B 23/00* (2006.01)
*G08B 21/02* (2006.01)
(Continued)

(52) U.S. Cl.
CPC ............ *G08B 21/02* (2013.01); *A61B 5/14551* (2013.01); *A61B 5/746* (2013.01); *G06F 19/345* (2013.01); *G06F 19/3418* (2013.01); *G08B 21/04* (2013.01)

(58) Field of Classification Search
CPC ...... G08B 21/22; G08B 25/14; G08B 29/145; A61B 5/14551; A61B 5/0002; A61B 5/021
USPC ............ 340/573.1, 10.3, 10.51, 635, 636.19, 340/539.11, 506, 515; 365/145, 154, 156, 365/185.14, 192; 600/323, 300, 301, 481
See application file for complete search history.

(56) References Cited

U.S. PATENT DOCUMENTS 4,365,636 A 12/1982 Barker
6,503,206 B1 * 1/2003 Li et al. ........................ 600/481
(Continued)

FOREIGN PATENT DOCUMENTS

WO 2011007271 A1 1/2011

OTHER PUBLICATIONS

Aboukhalil, A., et al.; Reducing False Alarm Rates for Critical Arrhythmias Using the Arterial Blood Pressure Waveform; 2008; J. Biomed. Inform.; 41(3)442-451.
(Continued)

*Primary Examiner* — Hoi Lau

(57) ABSTRACT

A system (202) generates patient alarms using a stepped alarm scheme. The system (202) includes one or more processors (220) programmed to receive physiological scores and/or physiological parameter values; compare the physiological scores and/or the physiological parameter values to a plurality of alarm levels; in response to a physiological score and/or physiological parameter value falling within an uninhibited zone of the alarm levels, issue an alarm; and set a first inhibition period for the uninhibited alarm level after issuing the alarm.

20 Claims, 16 Drawing Sheets

(51) Int. Cl.
  *A61B 5/1455* (2006.01)
  *A61B 5/00* (2006.01)
  *G06F 19/00* (2011.01)
  *G08B 21/04* (2006.01)

(56) References Cited

U.S. PATENT DOCUMENTS

| | | | |
|---|---|---|---|
| 7,880,626 B2* | 2/2011 | Al-Ali et al. | 340/635 |
| 8,131,583 B1* | 3/2012 | Rapposelli-Manzo | 705/7.41 |
| 8,882,666 B1* | 11/2014 | Goldberg et al. | 600/301 |
| 8,890,702 B2* | 11/2014 | Caby et al. | 340/635 |
| 8,926,509 B2* | 1/2015 | Magar et al. | 600/301 |
| 8,928,479 B2* | 1/2015 | Gonsalves et al. | 340/539.11 |
| 8,947,233 B2* | 2/2015 | Butler et al. | 340/572.1 |
| 2003/0092974 A1* | 5/2003 | Santoso et al. | 600/300 |
| 2007/0232880 A1 | 10/2007 | Siddiqui et al. | |
| 2008/0183054 A1* | 7/2008 | Kroeger et al. | 600/301 |
| 2009/0326340 A1 | 12/2009 | Wang et al. | |
| 2010/0280396 A1 | 11/2010 | Zhang | |
| 2011/0201905 A1* | 8/2011 | Spencer | 600/301 |

OTHER PUBLICATIONS

Curtis, D. W., et al.; SMART—An Integrated Wireless System for Monitoring Unattended Patients; 2008; J. Am. Med. Inform. Assoc.; 15:44-53.

Tarassenko, L., et al.; Integrated Monitoring and Analysis for Early Warning of Patient Deterioration; 2006; British Journal of Anaesthesia; 97(1)64-68.

\* cited by examiner

| Score | 3 | 2 | 1 | 0 | 1 | 2 | 3 |
|---|---|---|---|---|---|---|---|
| Resp. Rate (/min) | | <8 | | 9-14 | 15-20 | 21-29 | >30 |
| Pulse (/min) | | <40 | 41-50 | 51-100 | 101-110 | 111-130 | >130 |
| Temp. (°C) | | <35 | | 35-38.4 | >38.5 | | |
| CNS | | | | Alert | Voice | Pain | Unresp. |
| Urine (ml/hr) | 0 | <30 | <60 | | >150 | | |
| Sys. BP (mmHg) | <70 | <40 | 71-80 | 101-199 | | >200 | |

STEPPED ALARM METHOD FOR PATIENT MONITORS

CROSS REFERENCE TO RELATED APPLICATIONS

This application is a national filing of PCT application Serial No. PCT/IB2012/051654, filed Apr. 4, 2012, published as WO 2012/140547 A1 on Oct. 18, 2012, which claims the benefit of U.S. provisional application Ser. No. 61/475,453 filed Apr. 14, 2011, and U.S. provisional application Ser. No. 61/578,493 filed Dec. 21, 2011, both of which are incorporated herein by reference.

The present application relates generally to patient monitoring. It finds particular application in conjunction with reducing patient alarms and will be described with particular reference thereto. However, it is to be understood that it also finds application in other usage scenarios, and is not necessarily limited to the aforementioned application.

Patient deterioration is often preceded by a period of abnormal vital signs. As such, clinicians often employ predictive systems to assess the likelihood of deterioration. Such systems include abnormality scoring system, such as early warning scores (EWS) and modified EWSs (MEWS) scoring systems. Abnormality scoring systems unify assessments of a plurality of physiological parameters, such as vital signs, into a unified unit system and combine the individual assessments so as to determine a patient risk, which may lead to preventable adverse events like cardiac arrest or death.

For a sample EWS scoring system (FIG. 1), a EWS is determined based on several vital signs using a table. When a vital sign is normal, it is assessed a score of zero. With increasing degrees of abnormality of each vital sign, more points are assessed for the vital sign. The total score over all vital signs is an indication of abnormality, and, if it exceeds a preselected threshold, a follow up action is defined (e.g., a consultation by a clinician or activation of a so-called Rapid Response Team).

Clinicians typically perform abnormality scoring systems manually. However, one challenge with manually scoring is that the resources of medical institutions, such as hospitals, are limited. Therefore, patients in, for example, the general ward are infrequently assessed, typically once per 4-8 hours. Patients can deteriorate unnoticed in this sub-acute care setting. Late discovery of this deterioration can lead to unnecessary complications, intensive care unit (ICU) admission, cardiac arrest, death, and so on.

To alleviate this, automatic monitoring of patients is becoming increasingly prevalent. However, a principal challenge with automatic monitoring is alarm fatigue. Alarm fatigue is the condition in which clinicians become de-sensitized to clinical alarms because of the high probability that alarms are not of actual clinical significance.

One approach to reduce the alarm load is to raise alarm thresholds, typically manually. However, other nurses on the same shifts and subsequent shifts may not notice the high threshold and be lulled into a false sense of patient well being. Further, this reduces sensitivity and increases the likelihood of failing to detect patient deterioration. Another approach is to set an inhibition period after an alarm issues, so similar alarms are not issued until a rearming condition is met. In such an approach, the rearming condition is crucial to the reducing alarms.

The typical rearming condition is the passing of a predetermined inhibition period from the alarm triggering. This is based on the notion that any alarm following the first alarm is likely to be based on similar physiological data, and thus does not provide any additional information to the clinician. The clinician either is already planning to take action to treat the patient if he agrees with the alarm or he doubts the validity of the alarm. In either case, another alarm would be unnecessary. Thus, it is reasonable to inhibit further alarms for a limited period of time.

One disadvantage of this rearming condition is that additional alarms are not raised if the condition of a patient worsens within the alarm inhibition period. Another disadvantage is the predetermined amount of time is generic to a general patient population. As such, the predetermined amount of time is not tailored to any specific patient. Further, the predetermined amount of time does not adapt to an individual's dynamics.

Other challenges with automatic monitoring stem from predictive models typically employed by automatic monitoring systems. Such predictive models are typically trained on large databases of population data, whereby decisions using such predictive models are based on the general features of a large population. Further, differences between individuals and the general training population are typically not taken in to account. Training in this way can result in unnecessary alerts and/or failure to generate alerts for certain patients with physiological norms different from those of the general training population.

One solution is to adjust the predictive models based on knowledge of a patient's healthy, or baseline, physiological dynamics. However, baseline data is often not available in practice, particularly in an ICU, in which it can never be assumed that data being collected reflects the patient's "normal" physiology.

Another solution employs direct feedback from a clinician about the validity of an issued alarm for learning. However, such an approach is not possible for systems that do not have the benefit of this direct-feedback learning. Further, if alarms are issued in response to predicted events hours in advance, immediate feedback from a clinician about the validity of an alarm is meaningless.

The present application provides new and improved methods and systems which overcome the above-referenced problems and others.

In accordance with one aspect, a system for generating patient alarms using a stepped alarm scheme is provided. The system includes one or more processors programmed to receive physiological scores and/or physiological parameter values; compare the physiological scores and/or the physiological parameter values to a plurality of alarm levels; in response to a physiological score and/or a physiological parameter value falling within an uninhibited one of the alarm levels, issue an alarm; and set a first inhibition period for the uninhibited alarm level after issuing the alarm.

In accordance with another aspect, a method for generating patient alarms using a stepped alarm scheme is provided. Physiological scores and/or physiological parameter values are received. The physiological scores and/or physiological parameter values are compared to a plurality of alarm levels. In response to a physiological score and/or a physiological parameter falling within an uninhibited one of the alarm levels, an alarm is issued. Further, a first inhibition period is set for the uninhibited alarm level after issuing the alarm.

In accordance with another aspect, a system for rearming an inhibited alarm level is provided. The system includes one or more processors programmed to receive physiological scores and/or physiological parameter values. The physiological scores and/or the physiological parameter values are compared to a plurality of alarm levels. In response to a physiological score and/or physiological parameter value falling within an uninhibited one of the alarm levels, an alarm is issued. An inhibition period for the uninhibited alarm level is set and, in response to setting the inhibition period, the system waits a predetermined amount of time. A determination is made as to whether intervention measures were administered during the predetermined amount of time. In response to determining intervention measures were not administered and a current physiological score and/or physiological parameter value worsened by a predetermined amount compared to the physiological score and/or physiological parameter value, the inhibited alarm level is rearmed.

One advantage resides in increased sensitivity to abnormal patient conditions while reducing alarm loads.

Another advantage resides in sensitivity to absolute thresholds.

Another advantage resides in a low alarm load.

Another advantage resides in sensitivity to patient deterioration.

Another advantage resides in applicability to a single physiological parameter, as well as a plurality of physiological parameters.

Another advantage resides in intuitive parameters that are straightforward to tune.

Another advantage resides in minimizing bed-side modification of alarm thresholds.

Another advantage resides in adjusting to cases in which a patient has conditions that are not typical of the average population.

Still further advantages of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figures 1, 4:
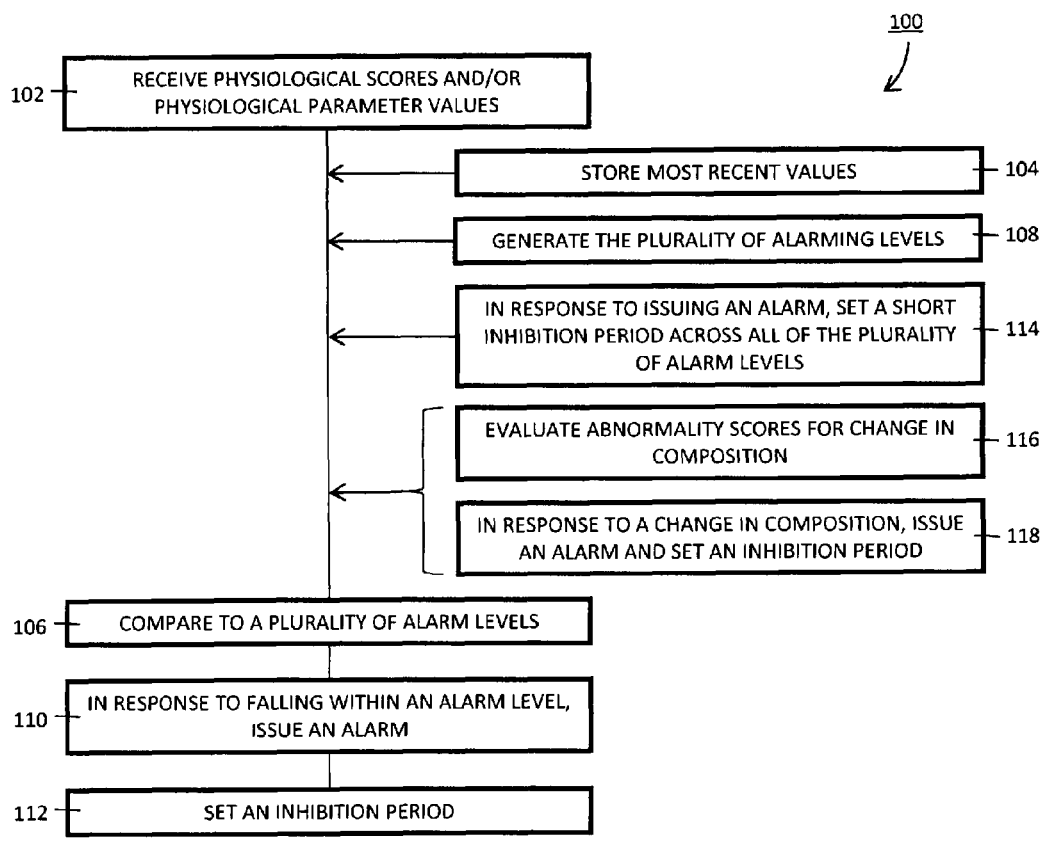
FIG. 1 is a table illustrative of a EWS scoring system.
FIG. 4 is a block diagram of a method of generating patient alarms according to aspects of the present disclosure.
Figure 2:
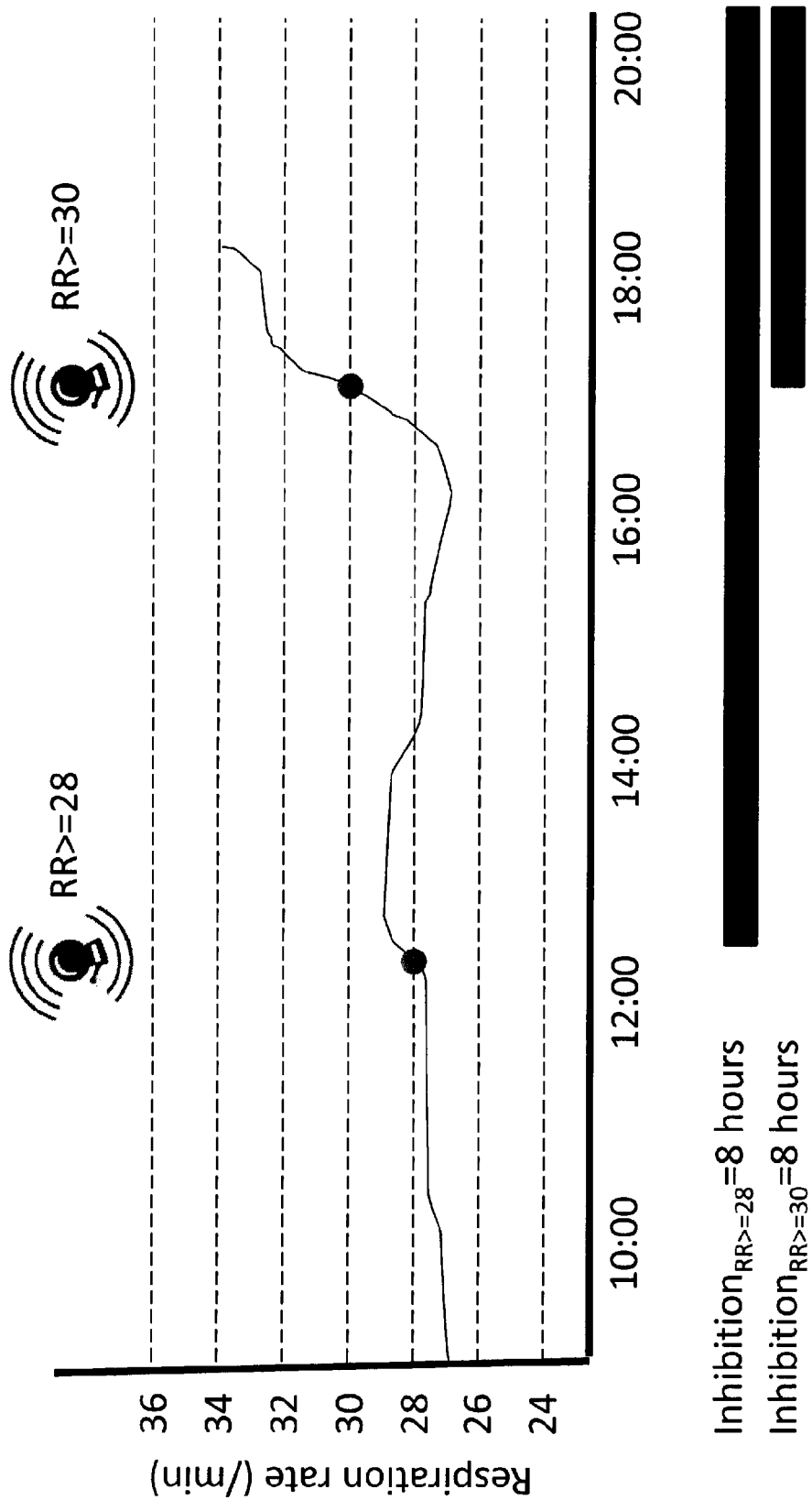
FIG. 2 is a graph illustrative of a method of generating patient alarms using measurements for a vital sign according to aspects of the present disclosure.
Figure 3:
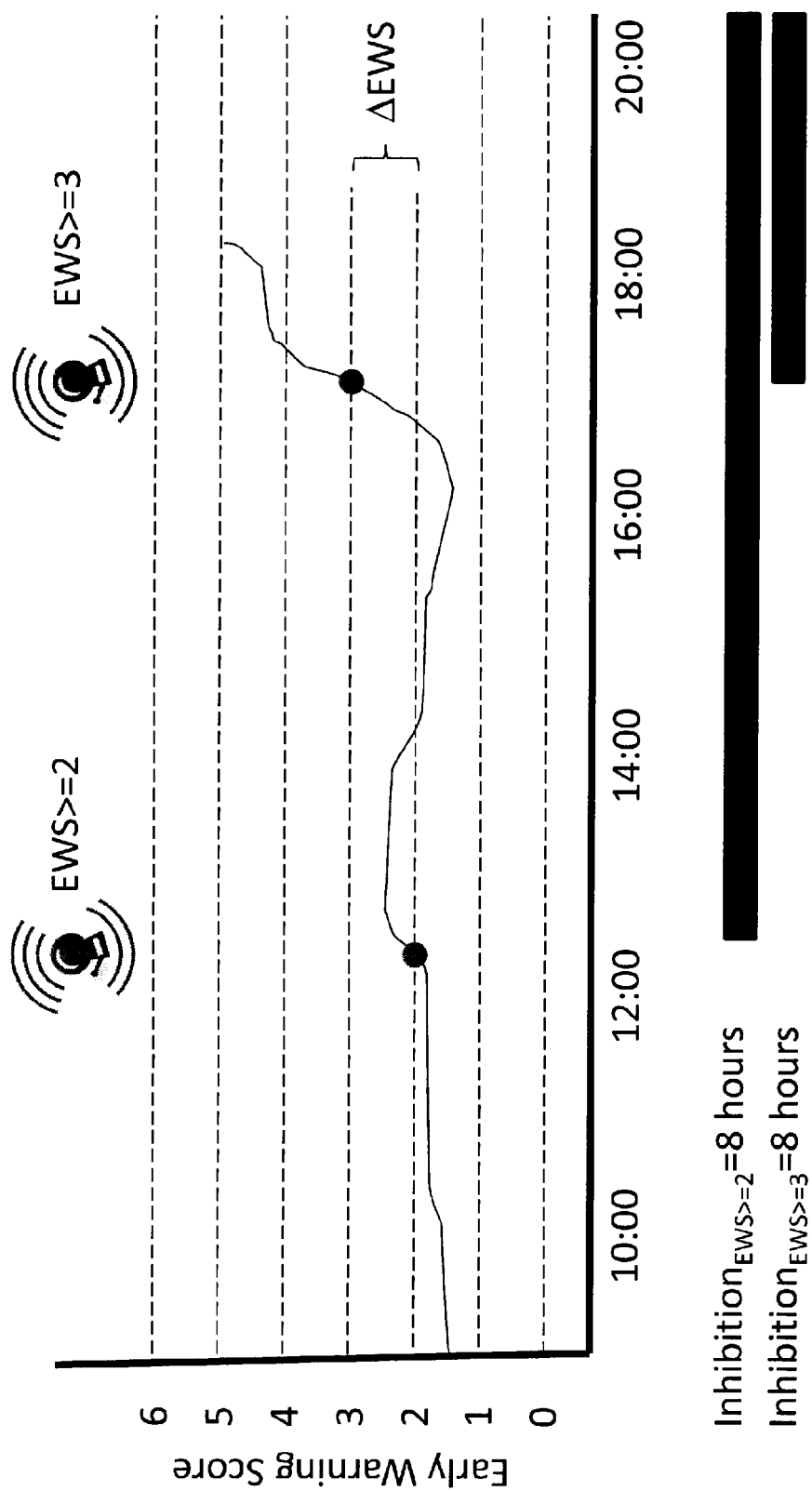
FIG. 3 is a graph illustrative of a method of generating patient alarms using abnormality scores according to aspects of the present disclosure.

With reference to FIGS. 2 and 3, illustrative examples of a method 100 (see FIG. 4) for generating patient alarms using a stepped alarm scheme are provided. Suitably, a patient monitor, such as a wearable patient monitor, a bedside patient monitor, and a central patient monitor, performs the method 100. As discussed in detail hereafter, by using a stepped alarm scheme in combination with long inhibition periods, fewer alarms are produced while still being sensitive to patient deterioration. FIG. 2 assesses patient deterioration using vital sign measurements for a single vital sign (e.g., respiration rate); whereas FIG. 3 assesses patient deterioration using an abnormality score (e.g., EWS) that can typically be calculated from a vital sign.

Vital sign measurements include measurements of vital signs, such as heart rate, temperature, blood oxygen saturation, level of consciousness, pain, urine output, and so on. Abnormality scores, such as EWS and MEWS, combine vital sign measurements for a plurality of vital signs into a score assessing the risk of death of a patient. Abnormality scoring systems provide a non-linear weighting to arrive at an "equally serious" rating scale for each vital sign. In that regard, all of the vital signs going into an abnormality score are assessed using this rating scale and summed to arrive at an abnormality score. Typically, the vital signs are assumed to be independent when calculating an abnormality score. However, some combinations of vital signs are more abnormal than others, whereby an abnormality score can further include scores for combinations of vital signs. To improve the sensitivity of an abnormality score for a vital sign, the vital sign can be weighted more heavily during the determination of the abnormality score. Additionally or alternatively, to improve the sensitivity, the scoring regions for the vital sign can be refined. It is contemplated that abnormality scoring systems can be tailored to individual patients, medical wards, medical institutions, and so on. In certain embodiments, a clinician tailors the abnormality scoring systems manually through use of user input devices. In other embodiments, the abnormality scoring systems are tailored automatically based on patient information from, for example, a patient information system.

In both examples of FIGS. 2 and 3, at roughly 12:30, an initial threshold is crossed. In the case of FIG. 2, the threshold is 28 breathes per minute, and, in the case of FIG. 3, the threshold is a EWS of 2. By exceeding the initial threshold, an alarm is issued, a long inhibition period, such as 8 hours, is applied for alarms of the same condition, and the threshold is raised. Thereafter, in both examples, at roughly 17:00, a second, higher threshold is crossed (i.e., the situation worsens). In the case of FIG. 2, the threshold is 30 breathes per minute, and, in the case of FIG. 3, the threshold is a EWS of 3. By exceeding the second threshold, another alarm is sounded, a long inhibition period, such as 8 hours, is applied for alarms of this new condition, and the threshold is raised.

With reference to FIG. 4, a block diagram of the method 100 for generating patient alarms using a stepped alarm scheme is provided. Physiological scores and/or physiological parameter values of one or more patients are received 102. A physiological score is an assessment of a physiological condition of a patient, such as hemodynamic stability or risk of death, based on at least one physiological parameter according to a physiological scoring system. A physiological parameter is a measurable or observable feature of a patient. Examples of physiological scores include abnormality scores, and examples of physiological parameters include vital signs.

Typically, the physiological scores and/or physiological parameter values are received automatically from sensors associated with the patients via, for example, a wired or wireless communications network. However, in other embodiments, the physiological scores and/or physiological parameter values are received manually from clinicians via, for example, user input devices. Further, the physiological scores and/or physiological parameter values are typically received continuously. However, the physiological scores and/or physiological parameter values can alternatively be received upon the occurrence of an event, such as a timer event (e.g., a periodic timer), a patient event, a manually triggered event (e.g., a clinician pressing a button), and so on. In certain embodiments, the physiological scores are received indirectly from the physiological parameter values. In that regard, the physiological scores are automatically calculated from the physiological parameter values. For example, EWSs are calculated from vital sign measurements as discussed above.

Figure 5:
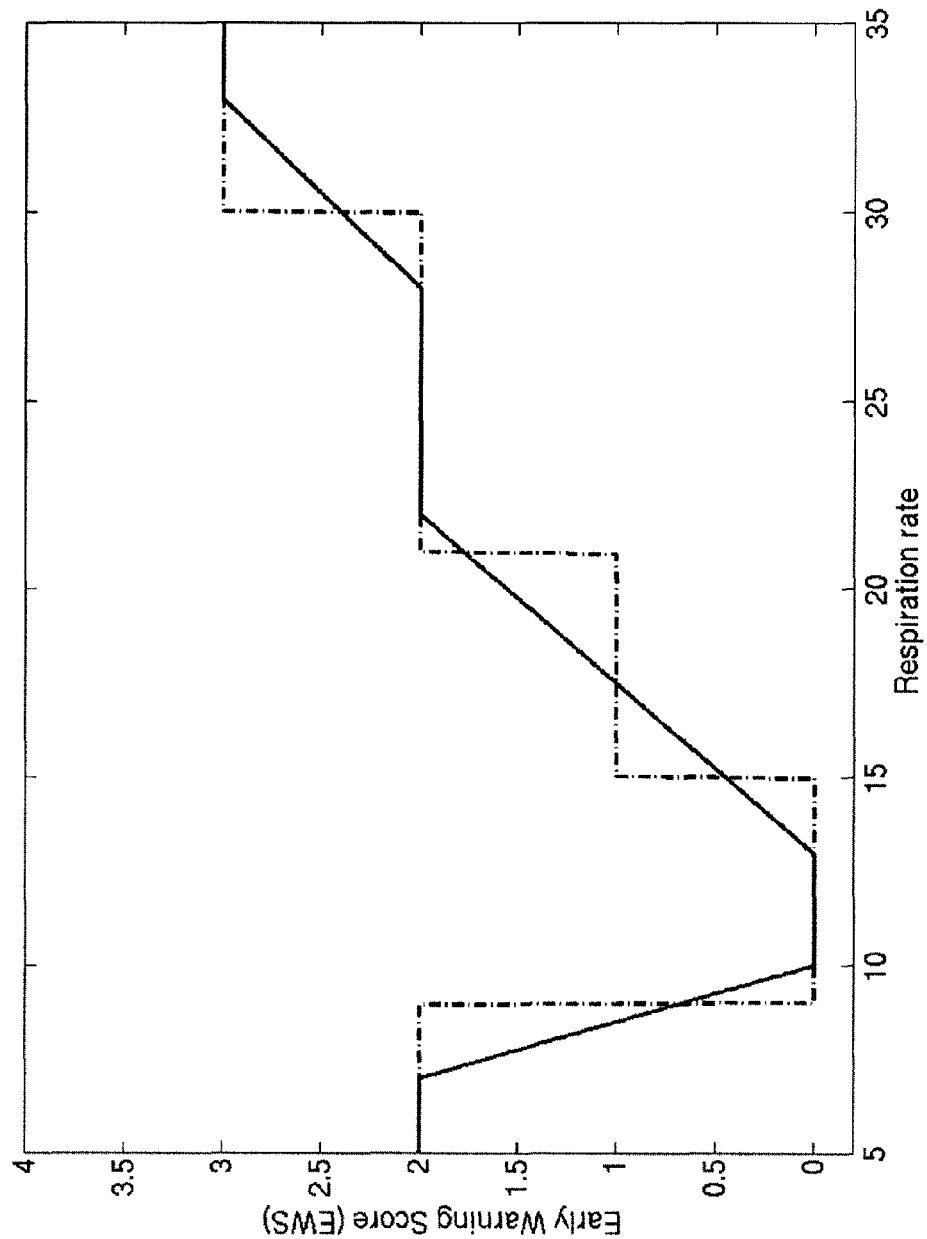
FIG. 5 is a graph illustrating a discrete and piecewise linearized EWS scoring system.

Abnormality scoring systems typically yield integer values. However, this can result in discrete jumps in abnormality scores, especially in cases when a vital sign is fluctuating around a border value. To alleviate this, abnormality scoring systems can be piecewise linearized. With reference to FIG. 5, an example of a piecewise linearized EWS scoring system for respiration rate is illustrated. The solid lines indicate a piecewise linearized version of the scoring system, and the dashed lines indicate a discrete version of the scoring system. In certain embodiments, a best fit approach is employed for linearization, although other approaches are contemplated.

Figure 6:
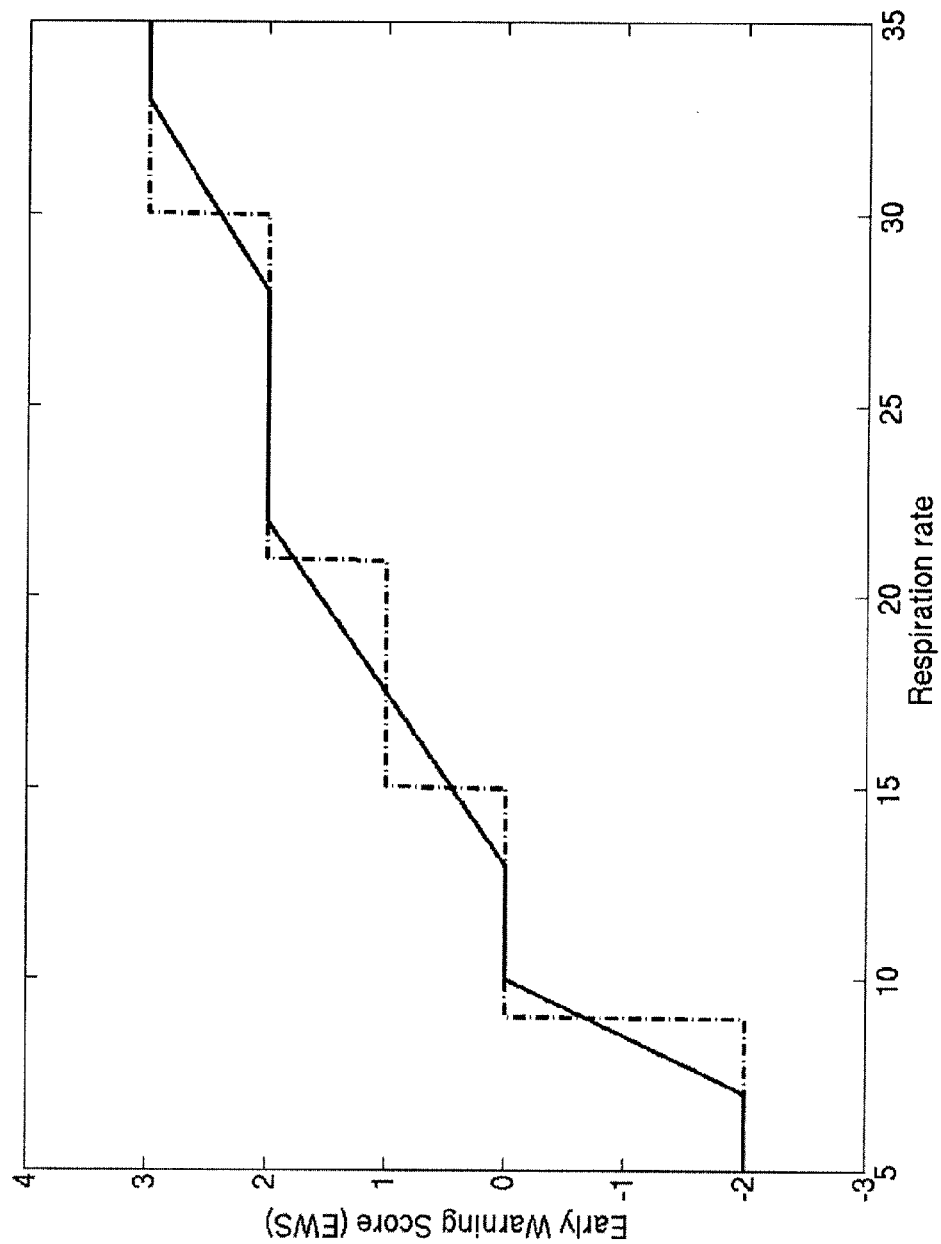
FIG. 6 is a graph illustrating a signed EWS scoring system (discrete and piecewise linearized).

Further, while individual scores attributed to vital signs in abnormality scoring systems are typically unsigned, it is contemplated that signed scores can be employed to distinguish between vital sign measurements for vital signs that are too low and too high. For example, such a distinction can be made by adding a plus ("+") and minus ("−") sign to scores for individual vital signs being too high and too low, respectively. With reference to FIG. 6, an example of signed abnormality scoring for respiration rate is illustrated. As in FIG. 5, the solid lines indicate a piecewise linearized version of the scoring system, and the dashed lines indicate a discrete version of the scoring system.

When calculating a physiological score, the situation can arise in which physiological parameter values for less than all the physiological parameters needed to calculate the physiological score are received. Physiological parameter values can be missing due to faulty measurements and/or observations, or can arise from differences in measurement and/or observation periodicity. For example, heart rate measured every minute and non-invasive blood pressure (NIBP) measured every 30 minutes. One solution to this situation is to store 104 the most recent physiological parameter values for each of the physiological parameters needed to calculate a physiological score in, for example, a memory. In that regard, physiological parameter values are used until a new physiological parameter value for the corresponding physiological parameter is received. Other solutions are to derive missing information from other physiological parameters (e.g., both ECG and SpO$_2$ can supply heart rate data) or a modeled combination of physiological parameters.

Referring back to FIG. 4, the physiological scores and/or physiological parameter values are compared 106 to a plurality of alarm levels. Alarm levels can include one or more of thresholds, ranges, and so on. Typically the alarm levels are determined by clinicians and/or defined by policy of the medical institution employing the method 100, such as a hospital. However, in certain embodiments, alarm levels can be dynamically generated 108. It is contemplated that alarm levels can be tailored to individual patients, medical wards, medical institutions, and so on. In certain embodiments, a clinician tailors parameters of the physiological scoring systems, such as thresholds of abnormality scoring systems, manually through use of a user input device. In other embodiments, the physiological scoring systems are tailored automatically based on patient information from, for example, a patient information system.

Figure 7:
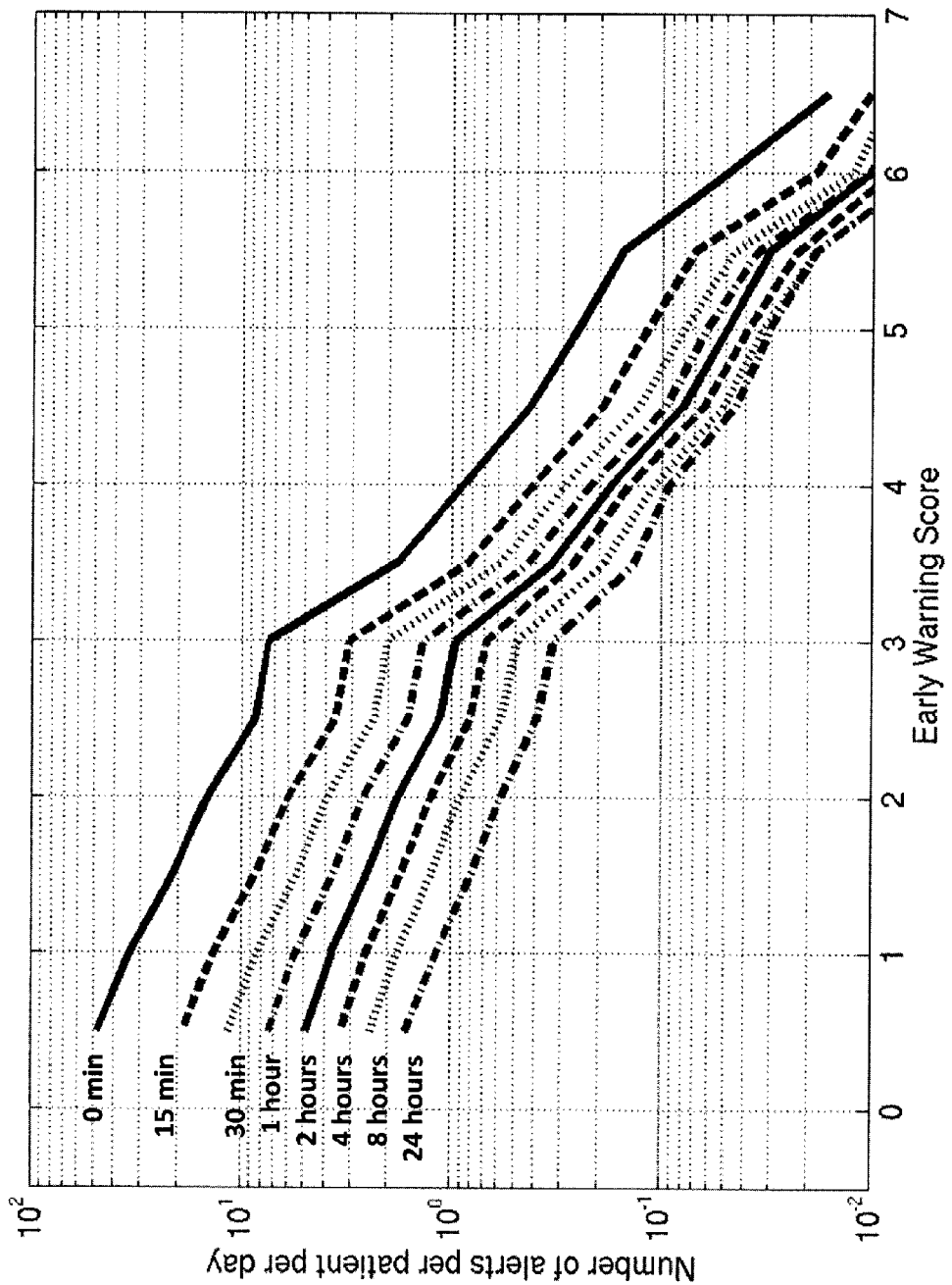
FIG. 7 is a graph illustrating a sample relation between alarm threshold and number of alarms per patient per day for different inhibition periods.

While no particular approach to selecting alarm levels is required, the alarm levels should be selected to minimize alarms while maximizing sensitivity to patient deterioration. With reference to FIG. 7, an example of the relation between alarm threshold for a EWS scoring system and average number of alarms per patient per day for different inhibition periods is provided. When a high alarm threshold and/or long inhibition period is chosen, the number of alarms is low. In contrast, when a low threshold is chosen, the method 100 becomes more sensitive for detection of abnormal vital signs. However, in combination with a long inhibition period, no alarm will be raised in case of further deterioration within the inhibition period.

One approach to dynamically generate 108 the alarm levels is through the use of a delta and an initial alarm level. For example, if a threshold of 3 for an abnormality score defines an initial alarm level and the delta is 0.5, an initial alarm will sound at 3.0 and another alarm will sound at 3.5, even when still within an inhibition period of the initial alarm level. After raising the other alarm, a new inhibition period for the 3.5 level is set, and another alarm level at 4 will be the next alarm level to trigger if the patient deteriorates further. The delta can be tailored to individual patients, medical wards, medical institutions, and so on. In certain embodiments, a clinician tailors the delta manually through use of a user input device. In other embodiments, the delta is tailored automatically based on patient medical records from, for example, a patient information system. For more severe patients (e.g., patient's with a higher abnormality score), a lower delta can be chosen to increase sensitivity to deterioration. After the inhibition period, the threshold is lowered.

Figure 8:
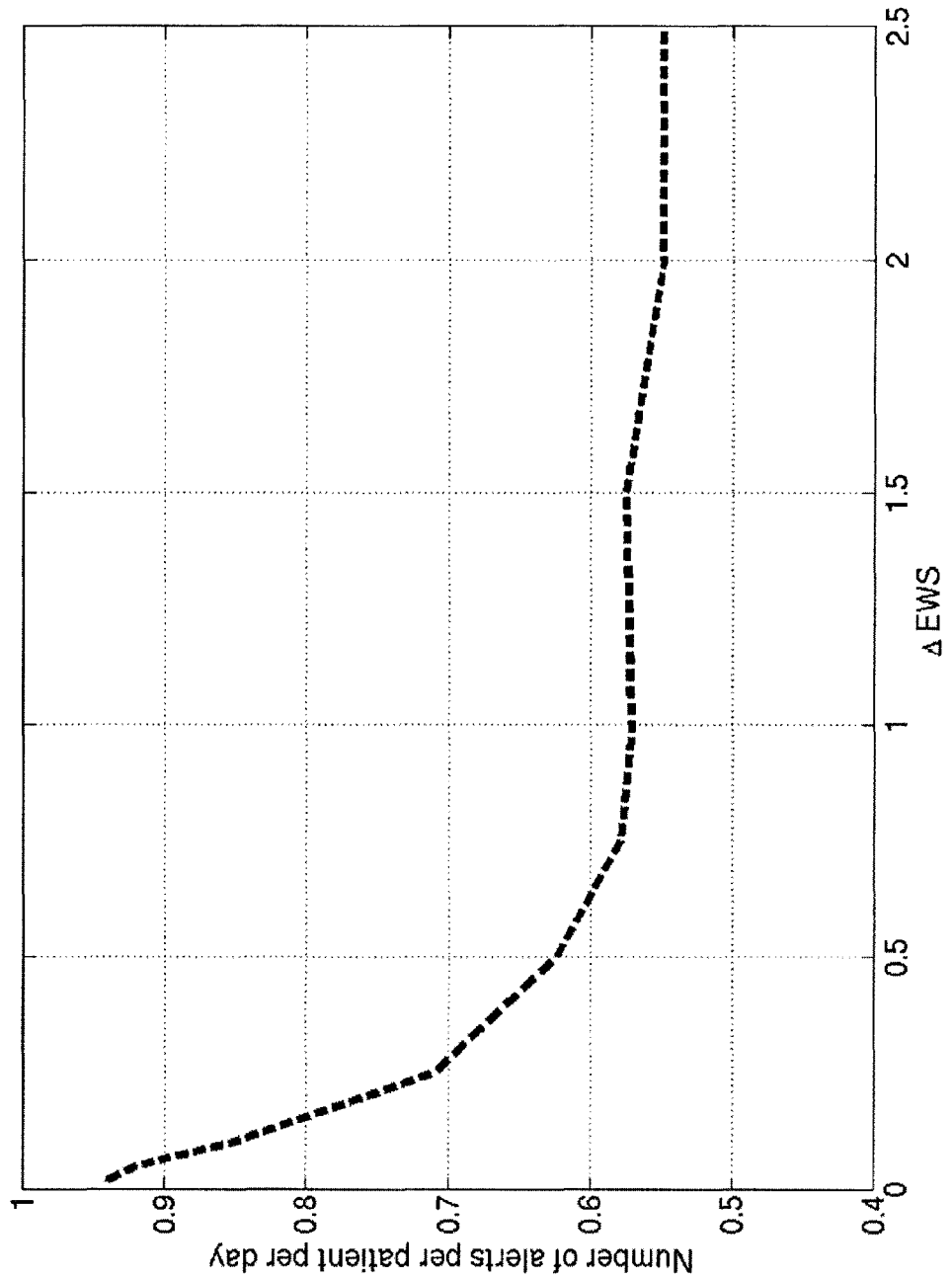
FIG. 8 is a graph illustrating a sample relation between a change in EWS versus alarms per patient per day.
Figure 9:
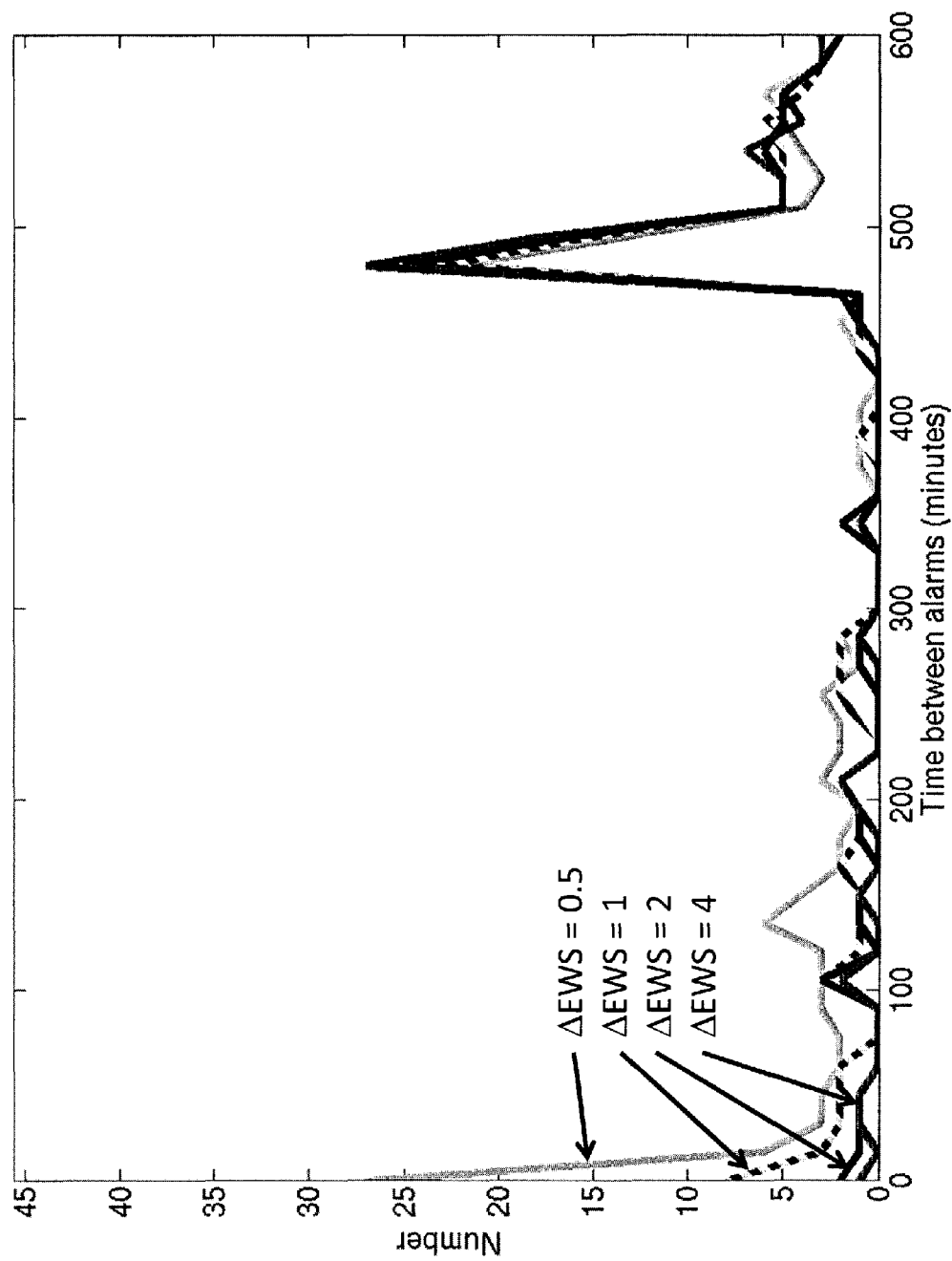
FIG. 9 is a graph illustrating a sample relation between alarms per patient per day and time between alarms for different ΔEWSs.

With reference to FIG. 8, a graph showing an example of the relation between delta for a EWS scoring system and number of alarms per patient per day. An important observation is that by implementing a delta, the method 100 is very sensitive to further worsening of patient condition while the average alarm load is minimally adversely influenced. Further, setting a delta too high will seldom trigger a new alarm, while setting it too small could cause bursts of alarms in a short period of time. One approach to assess reasonable values for a delta is by plotting time difference between alarms. Referring to FIG. 9, an example of such a plot for a EWS scoring system is illustrated. Therein, a large peak at 480 minutes is visible, which is a logical consequence from the chosen inhibition period of 480 minutes (8 hours). If a small value for delta (0.5) is chosen, a large peak at short times between alarms becomes visible, which is caused by quickly succeeding alarms during upward trends in the EWS. Based on visual inspection of generated events at the different settings, a reasonable value for delta is in the order of 1-2.

Referring back to FIG. 4, in response to a physiological score and/or physiological parameter value falling within an uninhibited one of the alarm levels 110, an alarm is generated. An alarm suitably notifies a clinician to check on a patient and, in certain embodiments, the severity of the alarm. Thereafter, a long inhibition period, such as on the order of a few hours, is set 112 for the triggered alarm level. In certain embodiments, the inhibition period suppresses alarms for lower alarm levels as well. To ensure clinicians don't miss alarms, the inhibition period is typically set only after the alarm is acknowledgement by, for example, a clinician. The length of the inhibition period can be variable between alarm levels. In certain embodiments, an inhibition period comparable to the duration of a nurse shift (e.g., 8 hours) is employed. Advantageously, this ensures that no alarm is raised for a patient condition that is unchanged during the shift, while a new nurse in the following shift is re-notified about the existing patient condition. In other embodiments, an inhibition period until the next nurse shift is employed. However, this has the drawback that numerous alarms will sound at the beginning of each nurse shift. In other embodiments, shorter inhibition periods for higher abnormality scores or vital sign measurements are employed.

In response to issuing an alarm 114, in certain embodiments, a short inhibition period across alarm levels is set. In other words, a short inhibition period suspending all alarms is set after issuing an alarm. Suitably, this short inhibition period is on the order of several minutes, such as 5-10 minutes. Advantageously, this reduces alarm load without significantly, if at all, compromising the well being of patients because the typical response time of a nurse in the general ward is in the order of several minutes.

Abnormality scores have the advantage of being a value that is easy to communicate. For example, 'patient x has a EWS of 6'. However, a drawback is that it no longer reveals what the contributions of the individual vital signs are. This leads to a risk of not detecting changes in the composition of an abnormality score, particularly in the presence of offsetting improvements of some vital signs and deterioration of others. This is undesirable because a constant abnormality score can incorrectly assess a situation as being stable notwithstanding that vital signs are fluctuating. Therefore, in certain embodiments, the composition of abnormality scores is evaluated 116 for changes in composition and, in response to composition changes 118, an alarm and inhibition period are triggered, as described above.

Figure 10:
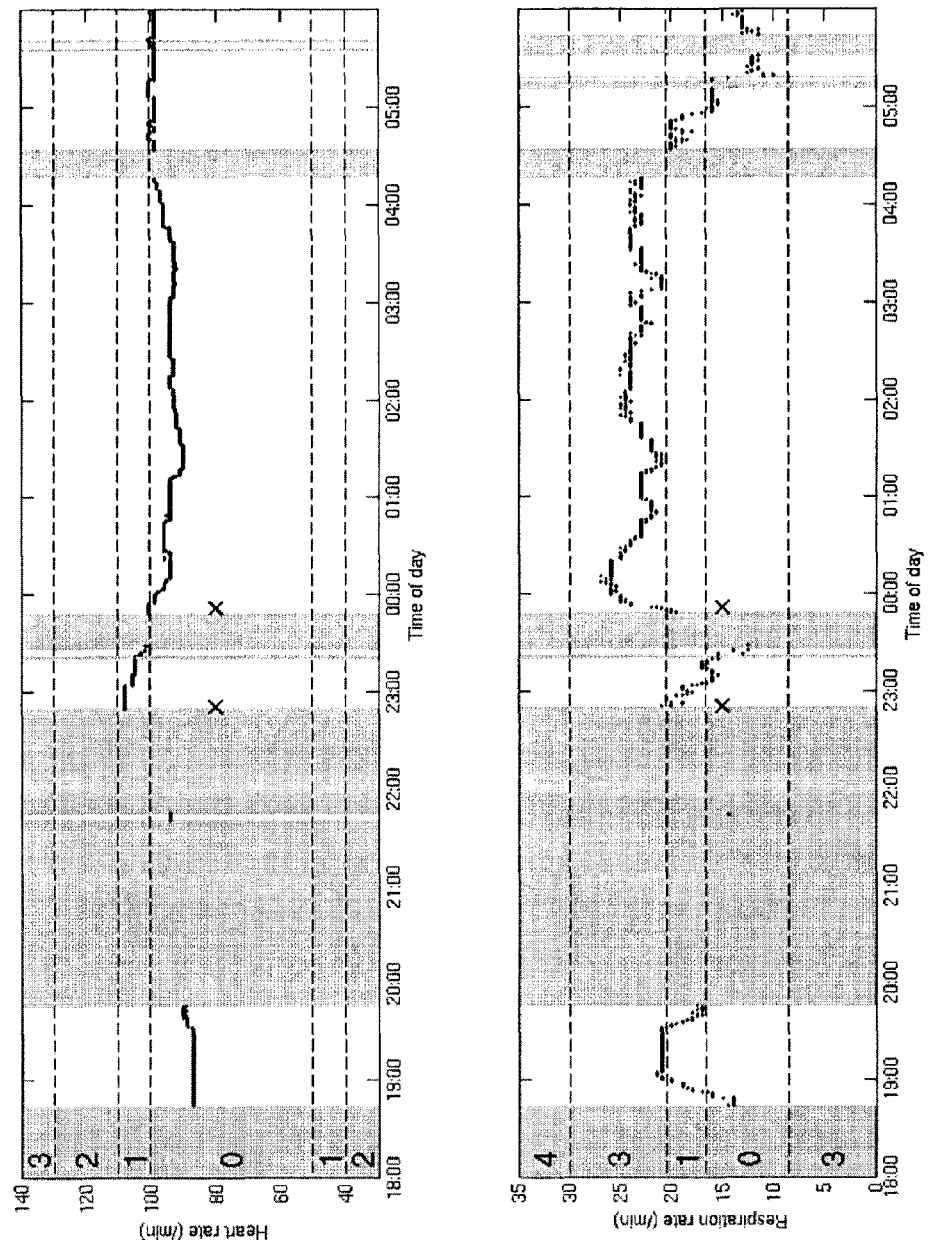
FIG. 10 is graphical depiction illustrating an unstable patient condition.

An example of a change in composition of an abnormality score (in this case EWS) derived from heart rate (HR) and respiration rate (RR) is shown in FIG. 10. Gray areas are periods of invalid data, and the crosses (x) denote alarms would have been raised. The dashed horizontal lines are the borders for the regions that score different numbers of 'EWS points'. The EWS points are indicated in large fontsize. A first alarm is raised around 23:00 hours due to HR, indicated by a cross in both graphs. Then, the HR improves somewhat, while the respiration rate degrades from being somewhat too high to being very much too high. The result is that the EWS remains the same. However, even so, there is an unstable situation, which justifies a new alarm.

Figure 11:
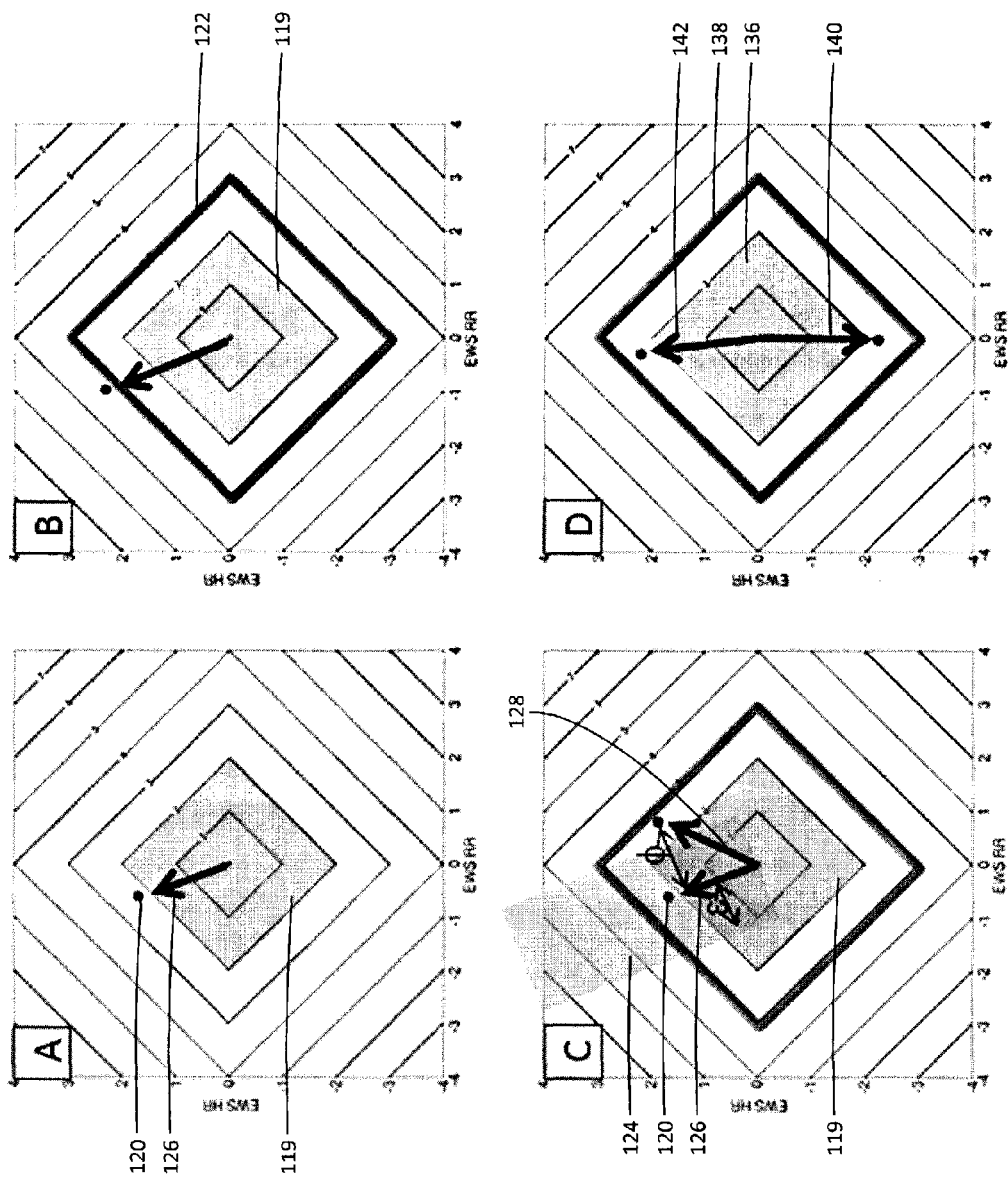
FIG. 11 is a graphical illustration of an approach to detecting an unstable patient condition.

One approach for evaluating 116 (FIG. 4) an abnormality score for changes in composition according to this example is explained using Subfigures A-C in FIG. 11. As will be seen below, the signed abnormality scoring of FIG. 6 finds particular application herein. Subfigures A-C show the case for a two dimensional abnormality score (i.e., EWS) based on, for example, respiration rate (RR) and heart rate (HR). Diagonal lines indicate constant abnormality scores. Further, a highlighted square region 119 represents the minimum alarm level that is set to generate an alarm (in this example a level of 2 is chosen).

Referring to Subfigure A, a dot 120 indicates a measurement scoring 0.5 points for the respiration being abnormally low (i.e., −0.5) and 1.7 points for the HR being abnormally high (i.e., +1.7). Thus, the total abnormality score is 2.2. After an alarm is triggered, a higher alarm level is automatically selected, as indicated by a highlighted box 122 in subfigure B. This example assumes a delta of 1.0. A highlighted rectangular region 124 (also referred to as the inhibition zone) in subfigure C indicates additional boundaries that are set to prevent the earlier mentioned problem of changes in composition that may go unnoticed. A score vector 126 of the last alarm (i.e., the alarm of Subfigure A) that was raised forms the axis of the highlighted rectangular region 124. If a current score vector 128 drifts outside of this region, a new alarm will sound, even when the next absolute alarm level (3.0 in this example) has not been raised. Detection of this drift is done by continuously checking the vector distance (I) between the current score vector 128 and the score vector 126 of the previous alarm. If this distance is larger than a defined, e.g., user set, level 8, an alarm will sound and the highlighted rectangular region 124 is redefined. This calculation of the distances can be done using standard vector algebra. This algebra remains essentially the same in case this approach is extended to more vital signs.

Figure 12:
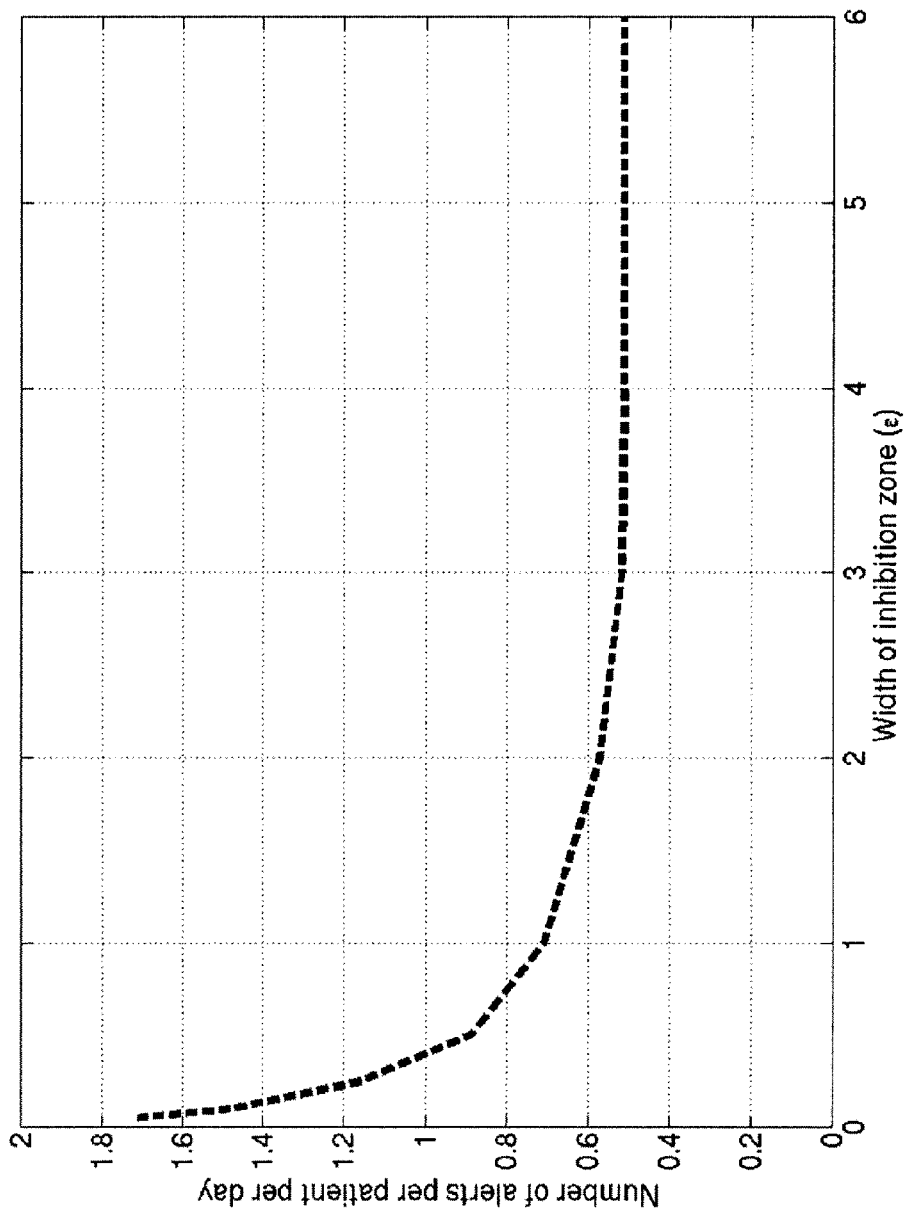
FIG. 12 is a graph illustrating a sample relation between width of an inhibition zone (ε) and number of alarms per patient per day.

With reference to FIG. 12, an example of the number of alarms as a function of distances is shown. The values are for an initial EWS of 3, a delta of 1, and an inhibition period of 480 min. As can be seen, if the distances is too high, the method 100 will be insensitive to changes in composition, and, if the distances is too low, the number of alarms will increase because the width of the highlighted rectangular region 124 becomes similar to the normal fluctuations in score vector composition. Based on FIG. 12 and also on visual inspection of some of the generated alarms, a reasonable value for the width of the highlighted rectangular region 124 is in the order of 1-4.

Figure 13:
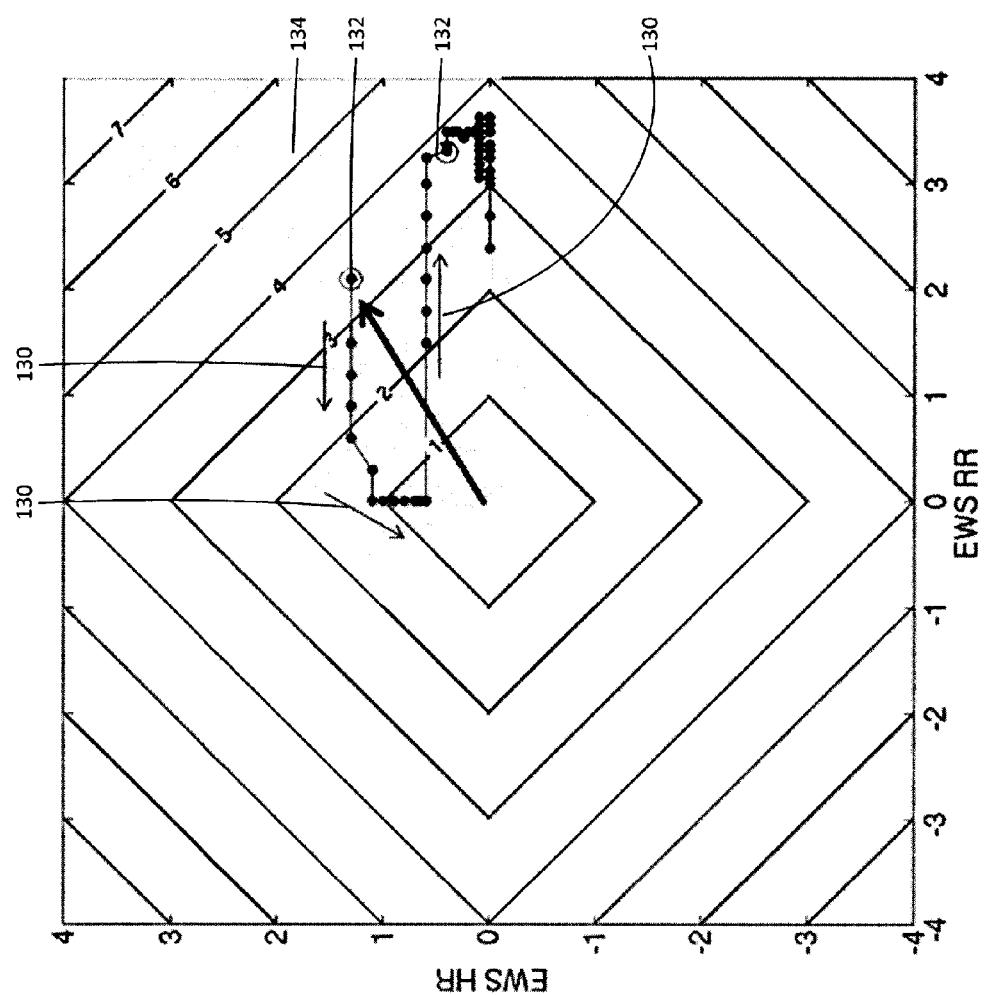
FIG. 13 is a graphical illustration of the unstable patient condition of FIG. 10 in EWS-space.

The example of FIG. 10 can also be plotted in 'EWS space', as shown in FIG. 13. The measurements are indicated by the interconnected dots, with the arrows 130 indicating the direction of time. The two alarms of FIG. 10 are indicated in this figure by circles 132. The highlighted rectangular region 134 (with a $\epsilon$ of 2) is the inhibition region, similar to the highlighted rectangular region 124 described above. Because of the large change in EWS composition, a new alarm is raised.

Figure 14:
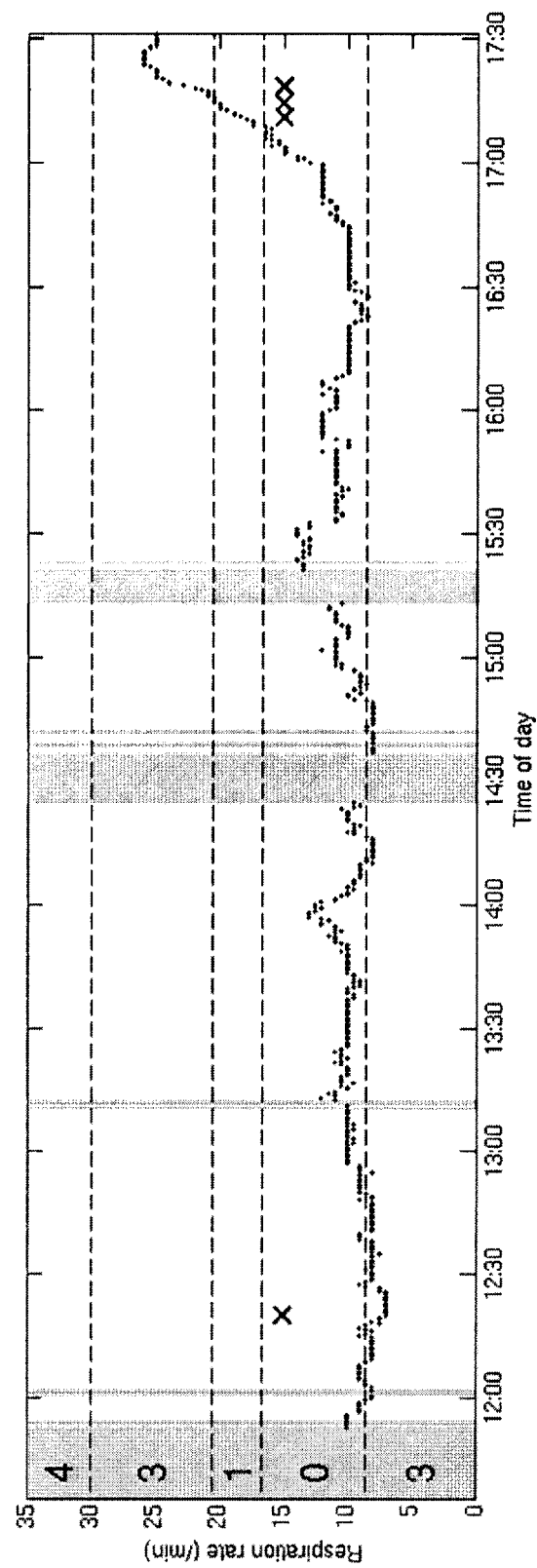
FIG. 14 is a graph illustrating a change in a sample patient's vital signs from being too high to too low.

Another example of a change in composition of an abnormality score (in this case EWS) derived from heart rate (HR) and respiration rate (RR) is shown in FIG. 14. Gray areas are periods of invalid data, and the crosses (x) denote the times an alarm would have been raised. The dashed horizontal lines are the borders for the regions that score different number of 'EWS points'. The EWS points are indicated in large fontsize. A first alarm is raised around 12:15 hours, indicated by a cross, because of an abnormally low respiration rate (scoring 3 EWS points). Around 17:15 hours the absolute EWS is still scoring less than 3 points, but the situation is unstable because the respiration is increasing rapidly. If no technical measures are taken, no alarm is issued because: 1) the previous alarm was less than 8 hours ago; 2) the EWS for respiration is still less than what was scored at 12:15 hours; and 3) the perpendicular distance Φ to the previous alarm vector is small.

Schematically, the foregoing situation is depicted in Subfigure D of FIG. 11. Subfigure D shows the case for a two dimensional abnormality score (i.e., EWS) based on, for example, respiration rate (RR) and heart rate (HR). Diagonal lines indicate constant abnormality scores. Further, a highlighted square region 136 represents the minimum alarm level that is set to generate an alarm (in this example a level of 2 is chosen), and a higher alarm level is indicated by a highlighted box 138. Even more, a current score vector 140 and a score vector 142 of the previous alarm are shown.

One approach for evaluating an abnormality score for changes in composition according to this example includes calculating the inner product between the current score vector 140 and the score vector 142 of the previous alarm. For an inner product <0 (rotation more than 90°) the inhibition period should be turned off so as to allow an alarm to be issued.

Figure 15:
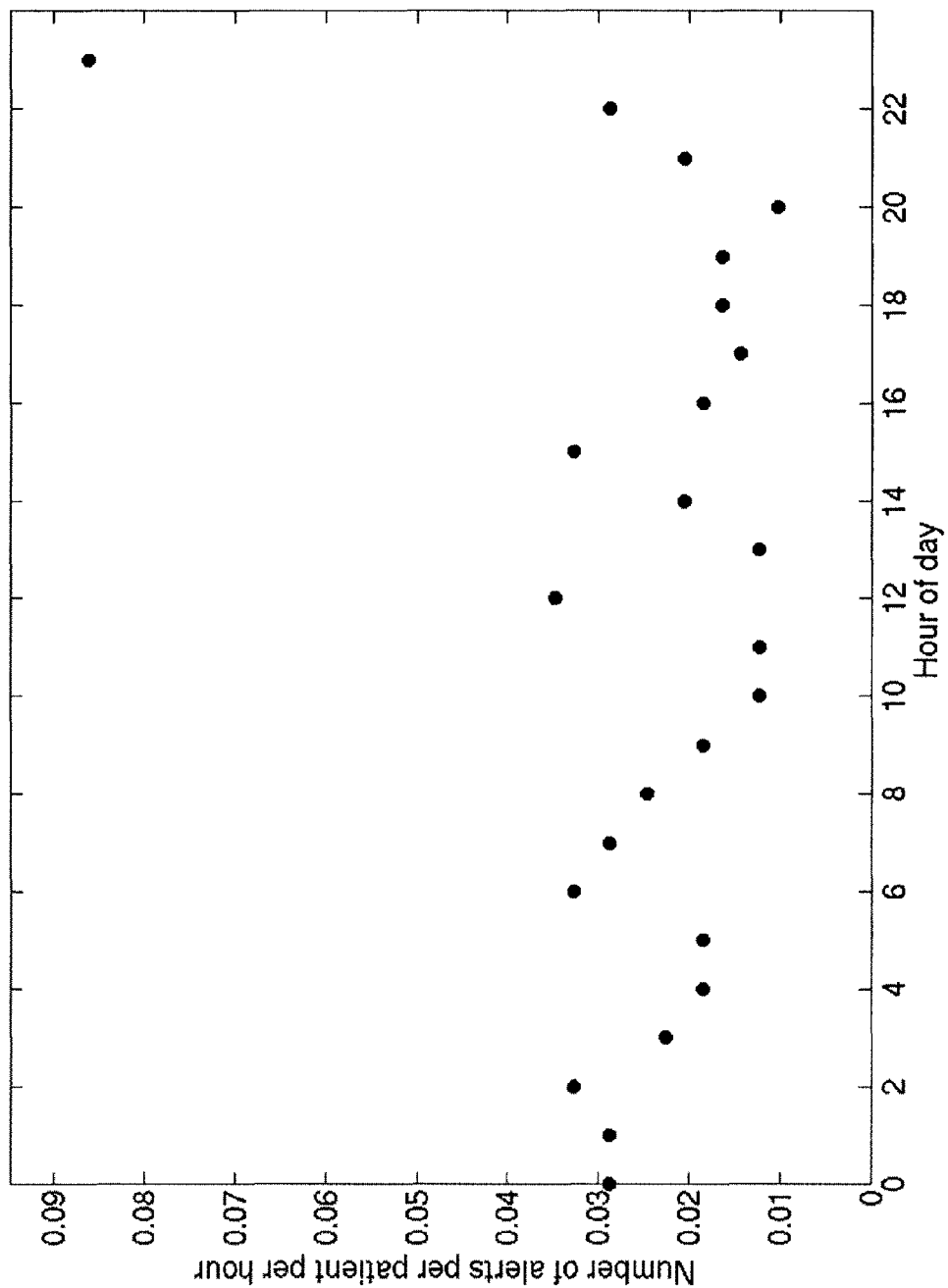
FIG. 15 is a graph illustrating the relation between number of alarms per patient per hour and hour of day.

With reference to FIG. 15, the low alarm load that results from the presented approach is shown. The initial alarm level is 3.0, the delta is 1.0, and the inhibition period is 8 hours. This results in an average alarm rate of approximately 0.02 alarms per patient per hour of the day. For a 25 bed ward this would be similar to about one alarm per 2 hours.

Figure 16:
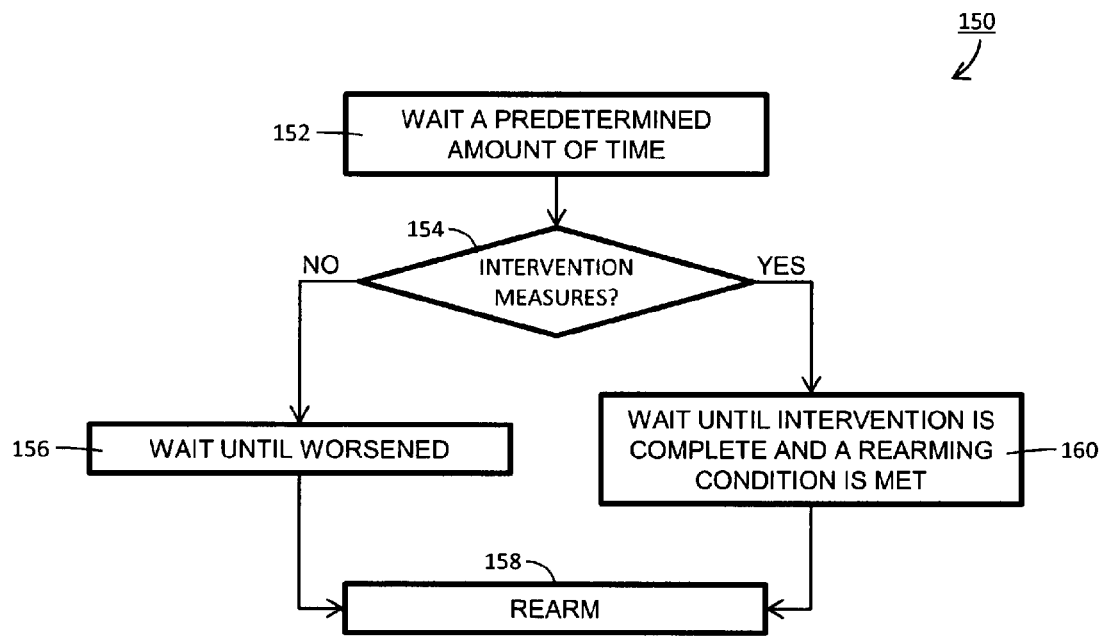
FIG. 16 is a block diagram of a method of rearming alarm levels according to aspects of the present disclosure.

The discussion heretofore dealt with re-arming alarm levels after a predetermined amount of time elapsed. For example, when a physiological score and/or physiological parameter value falls within an alarm level, an alarm is triggered and an inhibition period of a predetermined length is set inhibiting the same alarm level from triggering more alarms until the inhibition period ends. However, other approaches to rearming are contemplated. With reference to FIG. 16, a block diagram of an adaptive method 150 of rearming is provided.

The adaptive method 150 presupposes familiarity with the typical intervention measures taken by clinicians in response to alarms. For example, typical intervention measures taken in response to an alarm for hemodynamic stability include the administration of fluids, vasopressors, or packed red blood cells. Further, the adaptive method 150 presupposes at least one source of clinical data describing intervention measures taken by clinicians in response to alarms. For example, such a source can be a patient information system which clinicians provide data regarding intervention measures taken via a user input device. Even more, the adaptive method 150 presupposes alarms triggered by physiological scores and/or physiological parameter values reflect a patient's stability with regard to a physiological condition, such as hemodynamic stability or nutritional stability. When the foregoing are available, the adaptive method 150 can be employed for rearming.

When a physiological score and/or physiological parameter value of a physiological scoring system and/or physiological parameter falls within an uninhibited alarm level, an alarm is triggered and the alarm level is inhibited. In response to inhibiting the alarm level, the adaptive method 150 waits 152 a predetermined amount of time, such as three hours. Typically, the physiological scoring system and/or physiological parameter is predictive, such that alarms generated therefrom are triggered in advance of patient deterioration. The predetermined amount of time typically corresponds to this lead time and typically varies depending on the physiological condition of the physiological score and/or physiological parameter value. After the predetermined amount of time has passed, a determination 154 is made as to whether intervention measures were administered during the predetermined amount of time to address the alarm based on received clinical data. This can be based on actual knowledge that an intervention occurred or knowledge of typical past intervention measures of for the physiological condition of the physiological score and/or physiological parameter value.

If no intervention measures were administered, the adaptive method 150 waits 156 until a current physiological score and/or physiological parameter value of the physiological scoring system and/or physiological parameter has worsened 156 by a threshold amount compared to the physiological score and/or physiological parameter value at the time of the alarm. The threshold amount can be fixed or variable, such as half of the distance to a previous physiological score and/or physiological parameter value of the physiological scoring system and/or physiological parameter. Once the current physiological score and/or physiological parameter value has worsened, the alarm level is rearmed 158. By rearming in this way, the lack of intervention by a clinician after a significant time has passed is interpreted as an indication that the patient's condition at the time of the first alarm is acceptable, normal, or stable, for that particular patient. Therefore, even though the current physiological score and/or physiological parameter value is abnormal, or unstable, by population standards, the adaptive method learns that it is normal for this patient.

If intervention measures were administered, this is recognized as acknowledgement by clinicians and further alarms are unnecessary. The adaptive method 150 waits 160 until at least one rearming condition is met. Rearming conditions include a fixed period of time has passed, the current physiological score and/or physiological parameter value has worsened by a predetermined amount compared to the physiological score and/or physiological parameter value at the time of the alarm, the current physiological score and/or physiological parameter value has worsened by more than half of the distance from a previous physiological score and/or physiological parameter value, such as the physiological score and/or physiological parameter value at the time of the alarm, a physiological score and/or physiological parameter value of the physiological scoring system and/or physiological parameter has fallen below a fixed threshold at least once since the alarm, a physiological score and/or physiological parameter value of the physiological scoring system and/or physiological parameter has fallen below a threshold determined by the current boundaries for the alarm level, and a threshold based on the typical changes for the applied intervention. The rearming conditions can be employed singly or in combination with one another. Once intervention is complete and at least one rearming condition is met, the alarm level is rearmed 158.

In some embodiments, the physiological scoring system and/or physiological parameter is a vital signs index (VIX). VIX is a physiological scoring system that typically combines low-latency data, such as current physiological parameter values, and, optionally, high-latency data, such as laboratory test results, and/or static data, such as demographics, into a single value reflective of stability of a physiological condition of a patient, such as the patient's hemodynamic status, pulmonary stability, nutritional stability, and so on. VIX values can be calculated continuously and/or upon the happening of an event, such as a timer event, a user input event, the availability of new data, and so on. Further, in some embodiments, the VIX values are saved for historical analysis.

A VIX value for stability of a physiological condition is calculated by providing values for predictive variables to a VIX model that generates the VIX value based on the predictive variables. The predictive variables are one or more of vital signs, features extracted from the static data, such as ethnicity, and the like relevant to determining the stability of the physiological condition. The VIX values produced by the models are typically probabilities. For example, a VIX value typically ranges between 0 and 1, where the closer the value is to 1, the more likely the patient is to be unstable. The VIX models can employ any predictive model methodology, such as logistic regression, multinomial logistic regression, linear regression and support vector machine learning.

In some embodiments, the VIX models include a logistic regression model for hemodynamic stability with the form of:

$$VIX = \frac{1}{1+e^{-z}},$$

where $$z = \gamma + \beta_1 * SBP + \beta_2 * SI + \ldots$$

The model takes in to account SBP and SI, which are highly significant predictive variables in determining hemodynamic stability, returns a VIX between zero and one. The higher the VIX, the less stable the patient. In some embodiments, $\beta_1$, the coefficient for SBP, is negative. As SBP gets lower, VIX tends to increase, reflecting that the patient is approaching a less stable state. Further, $\beta_2$, the coefficient for SI, is positive. As SI gets higher, VIX also tends to increase, again reflecting a decrease in stability.

Figure 17:
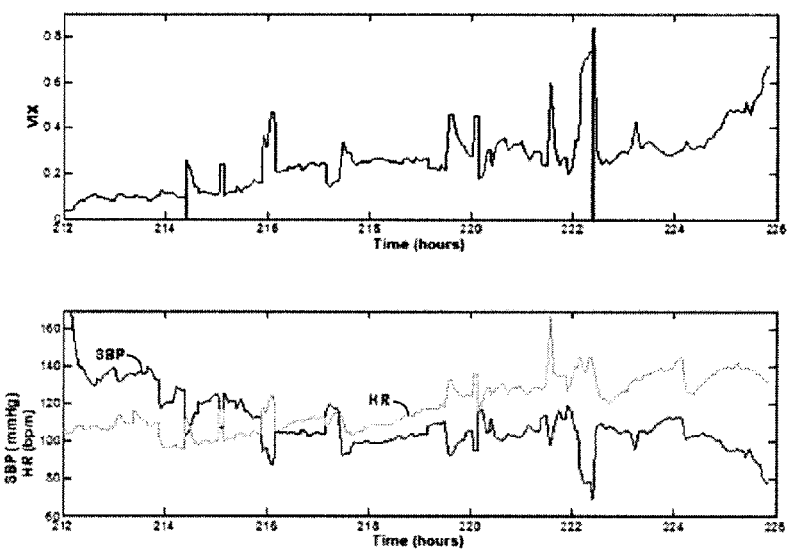
FIG. 17 is a graphical illustration of rearming of an alarm level.

With reference to FIG. 17, a plot of the VIX for a patient and the corresponding inputs, SBP and HR, over the course of several hours is illustrated. An alert is generated at hour 214.5 as the VIX value of the patient crosses the alert threshold. During the course of the three hours that follows the first alert, no intervention is taken. This is interpreted to mean that the patient's dynamics at the time of the first alert are normal, or acceptable, for that particular patient. Therefore, after three hours have passed, no alert is generated because the patient's VIX is not much higher than it was at the time of the first alert. By the time hour 222.5 is reached, however, VIX has significantly increased and, therefore another alert is issued for the patient. It should be noted that at hour 226, the clinician administered vasopressor indicating that, indeed, the patient experienced a clinically notable incident of hemodynamic instability.

In some embodiments, the physiological scoring system and/or physiological parameter is a baseline VIX (bVIX). bVIX is a physiological scoring system that indicates how a VIX has been behaving over a past predetermined amount of time, such as three hours. Many methods can be used to estimate the trend in a series of VIX values. Some are more sophisticated than others. In one embodiment, a bVIX value is the maximum VIX value or the 90 percentile VIX value within the past predetermined amount of time.

In view of the foregoing, by interpreting clinical data regarding intervention measures being implemented by the attending clinician, or lack thereof, in the context of the patient's condition upon the issuing of the first alarm, a method of rearming sensitive to a patient's individual physiological differences is provided. The method can suitably be employed to create a predictive alarm system that can learn and adapt to an individual's dynamics in the absence of direct clinician feedback.

Figure 18:
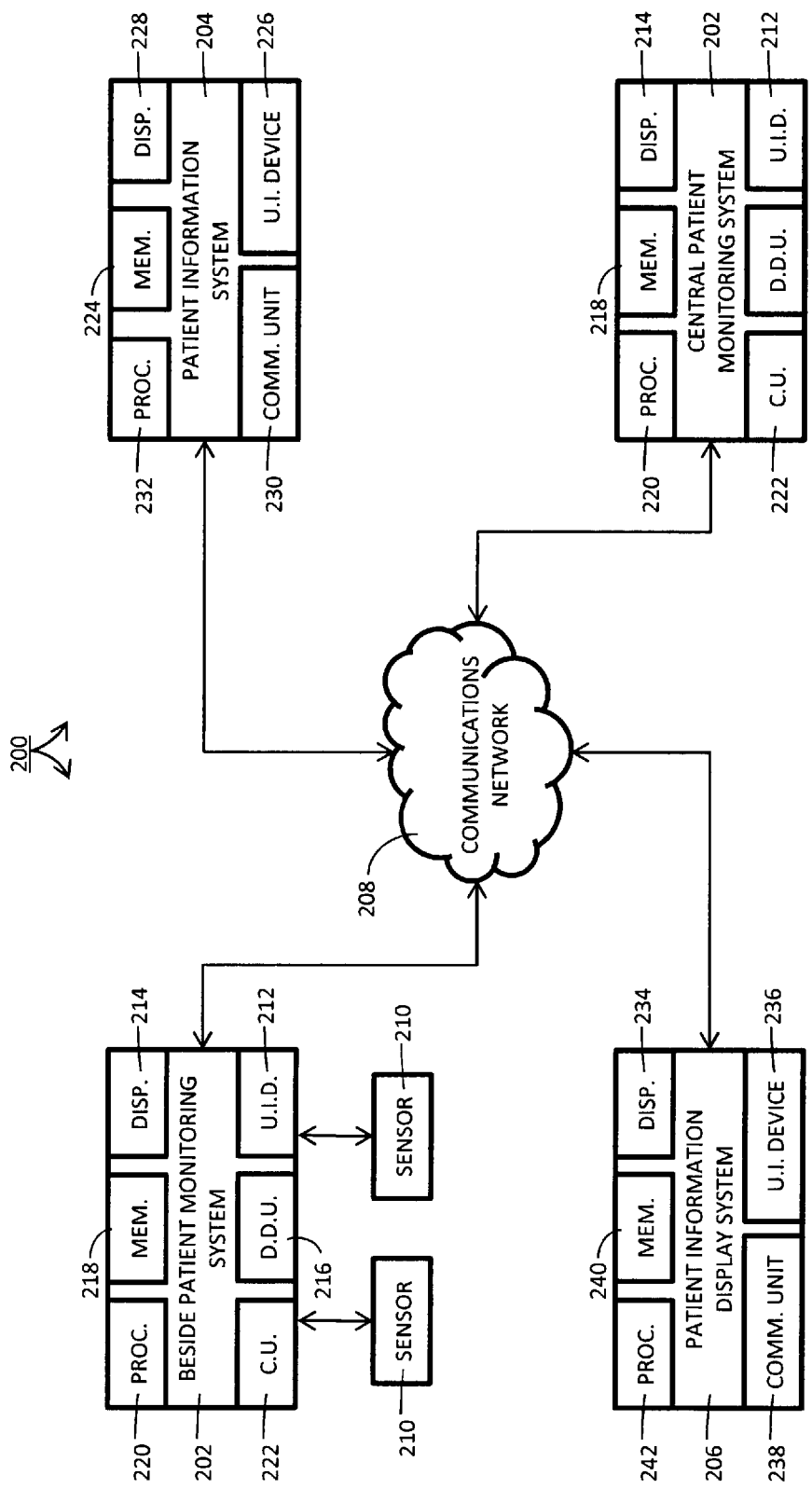
FIG. 18 is a block diagram of an IT infrastructure according to aspects of the present disclosure.

With reference to FIG. 18, a block diagram illustrates one embodiment of an information technology (IT) infrastructure 200 of a medical institution, such as a hospital. The IT infrastructure 200 includes one or more bedside or spot-check patient monitoring systems 202, a patient information system 204, one or more patient information display systems 206, and the like, interconnected via a communications network 208. It is contemplated that the communications network 208 includes one or more of the Internet, a local area network, a wide area network, a wireless network, a wired network, a cellular network, a data bus, and the like.

The patient monitoring systems 202 receive physiological scores and/or physiological parameter values for patients (not shown) cared for by the medical institution. Typically, the patient monitoring systems 202 receive physiological scores and/or physiological parameter values automatically collected via, for example, one or more sensors 210, such as electrocardiographic (ECG) electrodes, blood pressure sensors, $SpO_2$ sensors, pulse sensors, thermometers, respiratory sensors, exhaled gas sensors, noninvasive blood pressure (NBP) sensors, and so on, and/or from other components of the IT infrastructure 200, such as lab equipment or other patient monitoring systems. However, the patient monitoring systems 202 can receive physiological scores and/or physiological parameter values manually collected from clinicians via, for example, user input devices 212. In certain embodiments, where the physiological scores and/or physiological parameter values are received from user input devices, a display 214 can be employed to facilitate such user input. The physiological scores and/or physiological parameter values are typically received continuously, but can alternatively be received upon the occurrence of an event, such as a timer event.

When a patient monitoring system receives physiological scores and/or physiological parameter values, a corresponding deterioration detection module 216 is employed to apply the method 100 for generating patient alarms using a stepped alarm scheme to detect patient deterioration. In certain embodiments, physiological scoring is tailored to patients based on patient information in the patient information system 204. Insofar as deterioration is detected, the patient monitoring system generates an alarm. In certain embodiments, the alarm is generated as an audio and/or visual warning via, for example, a corresponding display. In other embodiments, notification of patient deterioration is provided to another component of the IT infrastructure 200, such as one of the patient information display systems 206. Further, in certain embodiments, the method 150 of FIG. 16 is employed for rearming as opposed to the passing of a predetermined amount of time.

To carry out the above noted functionality, the patient monitoring systems 202 suitably include one or more memories 218 and one or more processors 220. Common examples of patient monitoring systems include patient wearable patient monitors, bed-side patient monitors, spot-check patient monitors and central patient monitors. The memories 218 store executable instructions for performing one or more of the above noted functions of the patient monitoring systems and suitably embody the deterioration detection modules 216. The processors 220 execute the executable instructions stored on the memories 218 to carry out the functions associated with the patient monitoring systems 202. Where the patient monitoring systems 202 are operative to communicate over the communications network 208, the patient monitoring systems 202 further include one or more communications units 222 facilitating communication between the processors 220 and the communications network 208.

The patient information system 204, such as a central record medical database, typically acts as a central repository of patient information including, for example, electronic medical records (EMRs). Additionally or alternatively, the patient information system 204 receives and stores one or more of physiological scores, physiological parameter values and clinical data for the patients in one or more memories 224 thereof. Typically the physiological parameter values and/or physiological scores are received from components of the IT infrastructure 200 via, for example, the communications network 208, but said measurements can be manually entered via one or more user input devices 212, 226. As to the latter, a user interface presented via a display 228 can facilitate such manual entry. The patient information system 204 further allows components of the IT infrastructure 200 to access stored data, such as the EMRs and/or physiological parameter values for patients, via the communications network 208.

To carry out the above noted functionality, the patient information system 204 suitably includes one or more communications units 230, the memories 224, and one or more processors 232. The communications units 230 facilitate communication between the processors 232 and the communications network 208. The memories 224 store executable instructions for controlling the processors 232 to perform one or more of the above noted functions of the patient information system 204. The processors 232 execute the executable instructions stored on the memories 224.

The patient information display systems 206 receive physiological scores and/or physiological parameter values for the patients cared for by the medical institution over the communications network 208 from a component of the IT infrastructure 200. Additionally or alternatively, the patient information display systems 206 receive alarms for the patients cared for by the medical institution. Using the received data, the patient information display systems 206 update associated displays 234 to graphically present the data to clinicians and/or generate alarms. As to the latter, audio and/or visual alarms via, for example, the displays 234 are contemplated. Further, in certain embodiments, user input devices 236 of the patient information display systems 206 are employed to acknowledge alarms to the component of the IT infrastructure 200 generating the alarm.

To carry out the above noted functionality, the patient information display systems 206 suitably include one or more communications units 238, one or more memories 240, and one or more processors 242. The communications units 238 facilitate communication between the processors 242 and the communications network 208. The memories 240 store executable instructions for controlling the processors 242 to perform one or more of the above noted functions of the patient information display systems 206. The processors 242 execute the executable instructions stored on the memories 240.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a user input device includes one or more of a mouse, a keyboard, a touch screen display, one or more buttons, one or more switches, one or more toggles, and the like; and a display includes one or more of a LCD display, an LED display, a plasma display, a projection display, a touch screen display, and the like.

The invention has been described with reference to the preferred embodiments. Modifications and alterations may occur to others upon reading and understanding the preceding detailed description. For example, although the methods and systems disclosed herein were made using the general ward population in mind, the alarm escalation can be applied to other healthcare settings as well, such as in ICU, emergency care or home monitoring. It is intended that the invention be constructed as including all such modifications and alterations insofar as they come within the scope of the appended claims or the equivalents thereof.

The invention claimed is:

1. A system for generating patient alarms using a stepped alarm scheme, said system comprising:
   one or more processors programmed to:
   receive physiological scores and/or physiological parameter values;
   compare the physiological scores and/or the physiological parameter values to a plurality of alarm levels;
   in response to a physiological score and/or physiological parameter value falling within an uninhibited zone of the alarm levels, issue an alarm; and,
   set a first inhibition period for the uninhibited alarm level after issuing the alarm, wherein an inhibition period is a period during which one or more corresponding alarm levels are inhibited from triggering an alarm, characterized in that the physiological score and/or physiological parameter value includes a vital signs index (VIX) value calculated from the physiological parameter values using a predictive model of stability of a physiological condition.

2. The system according to claim 1, wherein the physiological scores are calculated from the physiological parameter values.

3. The system according to claim 1, wherein the physiological scores are calculated using an abnormality scoring system, the abnormality scores based on a plurality of vital sign measurements of the physiological parameter values.

4. The system according to claim 3, wherein the abnormality scoring system is piecewise linearized.

5. The system according to claim 1, wherein the first inhibition period is set in response to acknowledgement of the alarm.

6. The system according to claim 1, wherein the processors are further programmed to:
   generate the plurality of alarm levels from an initial alarm level and a delta, wherein the plurality of alarm levels include the initial alarm level and one or more alarm levels of increasing severity, the alarm levels being spaced from the initial alarm level and other ones of the alarm levels by increments of the delta.

7. The system according to claim 1, wherein the processors are further programmed to:
   in response to issuing an alarm, set a second inhibition period across all of the plurality of alarm levels, the second inhibition period being shorter than the first inhibition period.

8. The system according to claim 1, wherein the processors are further programmed to:
   evaluate abnormality scores of the physiological scores for a change in composition; and,
   in response to the change in the composition of the abnormality scores, issue a second alarm; and,
   set an inhibition period for the uninhibited alarm level after issuing the second alarm.

9. A system for generating patient alarms using a stepped alarm scheme, said system comprising:
   one or more processors programmed to:
   receive physiological scores and/or physiological parameter values;

compare the physiological scores and/or the physiological parameter values to a plurality of alarm levels;
in response to a physiological score and/or physiological parameter value falling within an uninhibited zone of the alarm levels, issue an alarm; and,
set a first inhibition period for the uninhibited alarm level after issuing the alarm;
in response to at least one of a plurality of rearming conditions being met, rearming the uninhibited alarm level, the rearming conditions including:
a first rearming condition, which includes:
a predetermined amount of time passed;
no intervention was administered during the predetermined amount of time; and,
a current physiological score and/or physiological parameter value worsened by a predetermined amount compared to the physiological score and/or physiological parameter value; and,
a second rearming condition, which includes:
the predetermined amount of time passed;
intervention was administered during the predetermined amount of time; and,
a rearming condition is met.

10. The system according to claim 9, wherein the physiological score and/or physiological parameter value includes a vital signs index (VIX) value calculated from the physiological parameter values using a predictive model of stability of a physiological condition.

11. The system according to claim 9, wherein the physiological score and/or physiological parameter value includes a baseline vital signs index (VIX) value indicating a trend of a VIX over a past predetermined amount of time.

12. The system according to claim 1, further including at least one of:
one or more sensors measuring one or more vital signs of the physiological parameter values;
one or more user input devices receiving values of the physiological parameter values and/or the physiological scores; and,
a communications network exchanging physiological scores and/or physiological parameter values between the system and other components connected to the communications network;
wherein the physiological scores and/or the physiological parameter values are received from at least one of the sensors, the user input devices, and the communications network.

13. A method for generating patient alarms using a stepped alarm scheme, the method comprising:
receiving physiological scores and/or physiological parameter values;
comparing the physiological scores and/or the physiological parameter values to a plurality of alarm levels; and,
in response to a physiological score and/or physiological parameter value falling within an uninhibited zone of the alarm levels, issuing an alarm; and,
setting a first inhibition period for the uninhibited alarm level after issuing the alarm, wherein an inhibition period is a period during which one or more corresponding alarm levels are inhibited from triggering an alarm, characterized in that the physiological score and/or physiological parameter value includes a vital signs index (VIX) value calculated from the physiological parameter values using a predictive model of stability of a physiological condition.

14. The method according to claim 13, wherein the physiological scores are calculated from the physiological parameter values.

15. The method according to claim 13, further including:
evaluating abnormality scores of the physiological scores for changes in composition; and,
in response to a change in the composition of the abnormality scores, issuing an second alarm; and,
setting an inhibition period for the uninhibited zone of the alarm levels after issuing the second alarm.

16. The method according to claim 13, wherein the first inhibition period is set in response to acknowledgement of the alarm.

17. The method according to claim 13, further including:
generating the plurality of alarm levels from an initial alarm level and an increments delta, wherein the plurality of alarm levels include the initial alarm level and one or more alarm levels of increasing severity, the alarm levels spaced from the initial alarm level and other ones of the alarm levels by one or more of the increments delta.

18. The method according to claim 13, further including:
in response to at least one of a plurality of rearming conditions being met, rearming the uninhibited alarm level, the rearming conditions including:
a first rearming condition, which includes:
a predetermined amount of time passed;
no intervention was administered during the predetermined amount of time; and,
a current physiological score and/or physiological parameter value worsened by a predetermined amount compared to the physiological score and/or physiological parameter value; and,
a second rearming condition, which includes:
the predetermined amount of time passed;
intervention was administered during the predetermined amount of time; and,
a rearming condition is met.

19. A non-transitory computer readable medium carrying software which controls one or more processors to perform the method according to claim 13.

20. A system for rearming an inhibited alarm level, said system comprising:
one or more processors programmed to:
receive physiological scores and/or physiological parameter values;
compare the physiological scores and/or the physiological parameter values to a plurality of alarm levels;
in response to a physiological score and/or physiological parameter value falling within an uninhibited zone of the alarm levels, issue an alarm;
set an inhibition period for the uninhibited alarm level;
in response to setting the inhibition period, wait a predetermined amount of time;
determine whether intervention measures were administered during the predetermined amount of time;
in response to determining intervention measures were not administered and a current physiological score and/or physiological parameter value worsened by a predetermined amount compared to the physiological score and/or physiological parameter value, rearm the uninhibited alarm level.

* * * * *